United States Patent
Krämer et al.

(10) Patent No.: US 6,602,424 B1
(45) Date of Patent: Aug. 5, 2003

(54) SAFETY DEVICE FOR A BLOOD TREATMENT MACHINE AND A METHOD OF INCREASING THE SAFETY OF A BLOOD TREATMENT MACHINE

(75) Inventors: Matthias Krämer, Friedrichsdorf (DE); Carsten Müller, Euerbach (DE); Christian Johner, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/469,605

(22) Filed: Dec. 22, 1999

Related U.S. Application Data

(63) Continuation of application No. 09/321,966, filed on May 28, 1999, now abandoned.

(30) Foreign Application Priority Data

May 28, 1998 (DE) .......................... 198 23 811

(51) Int. Cl.[7] .......................... B01D 61/22; B01D 61/18; A61M 1/34
(52) U.S. Cl. .......................... 210/739; 210/85; 210/86; 210/97; 210/143; 210/321.65; 210/645; 210/646; 210/650; 210/744; 210/929
(58) Field of Search .................................. 210/645, 646, 210/650, 739, 744, 929, 85, 86, 97, 103, 141, 143, 321.71, 138, 321.65; 364/130, 148.01, 528.01

(56) References Cited

U.S. PATENT DOCUMENTS

| 4,469,593 A | * | 9/1984 | Ishihara et al. | ............ 210/96.2 |
| 4,596,550 A | * | 6/1986 | Troutner | .................... 604/5.01 |
| 5,230,341 A | * | 7/1993 | Polaschegg | ................. 128/668 |
| 5,656,153 A | * | 8/1997 | Kameno et al. | ............... 210/97 |
| 6,423,022 B1 | * | 7/2002 | Roeher et al. | ............ 604/5.01 |

FOREIGN PATENT DOCUMENTS

| DE | 40 24 434 | 2/1992 |
| DE | 40 24 434 C2 | 2/1992 |
| DE | 42 39 937 C2 | 6/1994 |
| EP | 0 089 003 | 9/1983 |
| EP | 0 272 414 | 6/1988 |
| EP | 0 358 873 | 3/1990 |
| EP | 0 686 404 | 12/1995 |

* cited by examiner

Primary Examiner—John Kim
(74) Attorney, Agent, or Firm—Kenyon & Kenyon

(57) ABSTRACT

To increase the safety of an extracorporeal blood treatment machine which has control of the ultrafiltration rate as a function of the blood volume of the patient, the ultrafiltration rate UFR(t) during the treatment is monitored in a safety device. The safety device has a computer unit for determining an upper limit for the ultrafiltration rate $UFR_{lim}$ from the predetermined total ultrafiltrate volume $UFV_{tot}$ and the predetermined treatment time UFT. The safety device also has a monitoring unit with which the ultrafiltration rate is limited to the upper limit determined by the computer unit so that any risk to the patient is prevented even in the case of faulty blood volume control.

24 Claims, 4 Drawing Sheets

SAFETY DEVICE FOR A BLOOD TREATMENT MACHINE AND A METHOD OF INCREASING THE SAFETY OF A BLOOD TREATMENT MACHINE

This application is a continuation of application Ser. No. 09/321,966 filed May 28, 1999, now abandoned.

FIELD OF THE INVENTION

The present invention relates to a safety device for an extracorporeal blood treatment machine, in particular a hemodialysis machine, a hemofiltration machine or a hemodiafiltration machine and a method of increasing the safety of an extracorporeal blood treatment machine.

BACKGROUND INFORMATION

Various methods of surgical blood purification or blood treatment are used to remove substances that are usually eliminated with the urine and to withdraw fluid from patients with chronic renal failure. Diffuse mass transport is predominant in hemodialysis (HD), and convective mass transport through the membrane takes place during hemofiltration (HF). Hemodiafiltration (HDF) is a combination of both methods.

Removing excess body fluid by ultrafiltration is a part of dialysis therapy. This process usually leads to a reduction in the patient's blood volume. It the blood volume is reduced too much, symptomatic hypotension occurs, a frequent side effect of dialysis therapy. The tolerance of patients to volume reduction differs greatly from individual to individual: a drop in blood pressure occurs with a higher incidence in critical patient populations, such as diabetics and arteriosclerosis patients.

With current standard therapy, either a fixed ultrafiltration rate UFR or a fixed rate over time (UF profile) is preset. The reduction in blood volume is not measured, and only if problems occur is the ultrafiltration rate reduced manually. Optionally blood volume may be replaced by infusions.

It has been proposed that the patient's blood volume be monitored during the extracorporeal blood treatment and that the ultrafiltration rate be adjusted in such a way as to prevent a reduction in blood volume, which would not be tolerated in terms of the patient's circulatory stability. A technical prerequisite for this method is a sufficiently exact sensor technology for determination of the blood volume.

The volume to undergo ultrafiltration during the treatment, i.e., the total ultrafiltrate volume $UFV_{tot}$, and the ultrafiltration rate UFR, affect the fluid compartment of the body as well as circulatory regulation, as mentioned above. Therefore, the process of ultrafiltration and thus also blood volume regulation are critical with regard to safety. In uncontrolled withdrawal of fluid at the rate of several L/h, a critical blood volume in terms of circulatory regulation is reached after only a few minutes, causing a severe drop in blood pressure requiring intensive medical measures.

Because of the possibility of a malfunction of the sensors and of the blood volume regulation control algorithm, it to date could not be guaranteed that there would not be any greater risk for the patient with these blood monitoring methods than with standard therapies where the physician assumes responsibility for the selected ultrafiltration rate or the ultrafiltration profile. Therefore, the equipment available commercially has heretofore avoided regulating the ultrafiltration rate as a function of the patient's blood volume.

SUMMARY OF THE INVENTION

An object of the present invention is to create a safety device for an extracorporeal blood treatment machine which enables regulation of the ultrafiltration rate as a function of the blood volume without increasing the risk to the patient.

The present invention provides a safety device for an extracorporeal blood treatment machine, the treatment machine having a blood inlet line leading from the patient to the inlet of a first chamber of an exchange unit divided by a semipermeable membrane into a first and second chamber, and a blood outlet line leading from an outlet of the first chamber to the patient. An ultrafiltration device for withdrawing a predetermined total ultrafiltrate volume from the second chamber of the exchange unit at an ultrafiltration rate during a predetermined treatment time is provided, as is a measurement unit for determining the blood volume or a measurement quantity of the patient correlating with the blood volume. A control unit determines and controls an ultrafiltration rate as a function of the blood volume. The present invention is characterized in that the safety device has a computer unit for determining an upper limit for the ultrafiltration rate from the predetermined total ultrafiltrate volume and the predetermined treatment time and a monitoring unit for limiting the ultrafiltration rate controlled by the control unit to the upper limit when the ultrafiltration rate predetermined by the computer unit reaches the upper limit.

In addition, another object of the present invention is to indicate a method of increasing the safety of an extracorporeal blood treatment machine with a blood volume control.

The present invention also provides a method of increasing the safety of an extracorporeal blood treatment machine having a blood inlet line leading from the patient to the inlet of a first chamber of an exchange unit divided by a semipermeable membrane into a first and second chamber, a blood outlet line leading from an outlet of the first chamber to the patient, an ultrafiltration device for withdrawing a predetermined total ultrafiltrate volume from the second chamber of the exchange unit at an ultrafiltration rate during a predetermined treatment time, a measurement unit for determining the blood volume or a measurement quantity of the patient which correlates with the blood volume, and a control unit for controlling an ultrafiltration rate as a function of the blood volume. The method is characterized by the following process steps: determining an upper limit for the ultrafiltration rate from the predetermined total ultrafiltrate volume and the predetermined treatment time and limiting the ultrafiltration rate which is controlled by the control unit to the upper limit when the ultrafiltration rate predetermined by the computer unit reaches the upper limit.

The patient's safety is increased by the fact that the ultrafiltration rate controlled as a function of the blood volume by the control unit of the extracorporeal blood treatment machine is limited to an upper limit $UFR_{lim}$ which is determined by the preset total ultrafiltrate volume $UFV_{tot}$ and the preset treatment time UFT. Basing the upper limit value on the ultrafiltration rate and the treatment time creates high safety for the patient without too greatly limiting the range within which the ultrafiltration rate can be varied.

In a preferred embodiment, the average ultrafiltration rate UFRM, which is necessary to withdraw the predetermined total ultrafiltrate volume $UFV_{tot}$ within the treatment time UFT, is determined by forming the quotient of the predetermined total ultrafiltrate volume $UFV_{tot}$ and the predetermined treatment time UFT. The upper limit value $UFR_{lim}$ for the ultrafiltration rate UFR is then determined by multiplying the average ultrafiltration rate UFRM by a factor $\alpha$. The factor $\alpha$ is preferably greater than 1.5 and smaller than 2.3.

Another preferred embodiment provides for the range of allowable ultrafiltration rates to be reduced progressively toward the end of the treatment. A reduction in the upper limit value for the ultrafiltration rate as the treatment time increases is advantageous in particular when using control algorithms which tend to select greater ultrafiltration rates at the beginning of the treatment than at the end of the treatment as a function of the blood volume, so that in accordance with experience the ultrafiltration tolerance is greater at the beginning of treatment than at the end of treatment. The reduction in the upper limit for the ultrafiltration rate may be an explicit function of the treatment time elapsed or the quantity of fluid already subjected to ultrafiltration.

In a preferred embodiment, the upper limit for the ultrafiltration rate drops during the treatment from a value determined by multiplying the average ultrafiltration rate by a factor $\alpha$ to the average ultrafiltration rate, with the factor $\alpha$ preferably being between 1.5 and 2.3.

In another preferred embodiment, the upper limit for the ultrafiltration rate $UFR_{lim}$ is based on the fact that greater ultrafiltration rates should not be allowed when only a low residual volume is to be removed. Therefore, the residual ultrafiltration rate UFRR(t) at which the ultrafiltrate volume can be withdrawn at a given point in the time frame still available in the treatment time UFT is determined.

By multiplying the residual ultrafiltration rate by a factor $\alpha$, which is advantageously between 1.5 and 2.3, the upper limit $UFR_{lim}$ (t) at this time is then determined. Basing the upper limit for the ultrafiltration rate on the residual ultrafiltration rate leads to higher rates being allowed only when they are necessary for withdrawing the residual volume. In comparison with a linear drop in the upper limit for the ultrafiltration rate, this limit has an effect in particular when a large portion of the volume has already been removed, i.e., in the critical phase of approaching the dry weight. An additional reduction in the maximum allowed rate is achieved here.

Monitoring the ultrafiltration rate controlled by the control unit of the blood treatment machine not only has the goal of protecting the patient from unphysiologically high ultrafiltration rates but also ensures that the patient will reach the desired dry weight. If the ultrafiltration rate is limited to an upper limit, there is the possibility that the volume to be filtered cannot be withdrawn within the predetermined treatment period.

Therefore, in another preferred embodiment, a warning device is provided, having a comparator device for comparing the residual ultrafiltration rate UFRR(t) with the upper limit $UFR_{lim}$ and/or with the average ultrafiltration rate UFRM. After exceeding the average ultrafiltration rate UFRM and/or the upper limit $UFR_{lim}$, the warning device delivers a warning signal by which the nursing staff is alerted to the fact that there are problems in reaching the desired dry weight of the patient. The user then has an opportunity to extend the treatment time and/or reduce the target volume or tolerate smaller blood volumes than originally planned or to complete the treatment with the remaining average ultrafiltration rate without blood volume control.

Since the ultrafiltration rate is to be limited only on exceeding a lower limit, the monitoring unit of the safety device preferably has a comparator device for comparing the ultrafiltration rate controlled by the control unit with the lower limit value. The monitoring device restricts the ultrafiltration rate to the upper limit $UFR_{lim}$ only when the ultrafiltration rate is greater than the lower limit.

BRIEF DESCRIPTION OF THE DRAWINGS

Several embodiments of the present invention are explained in greater detail below with reference to the drawings in which.

DETAILED DESCRIPTION

Figure 1:
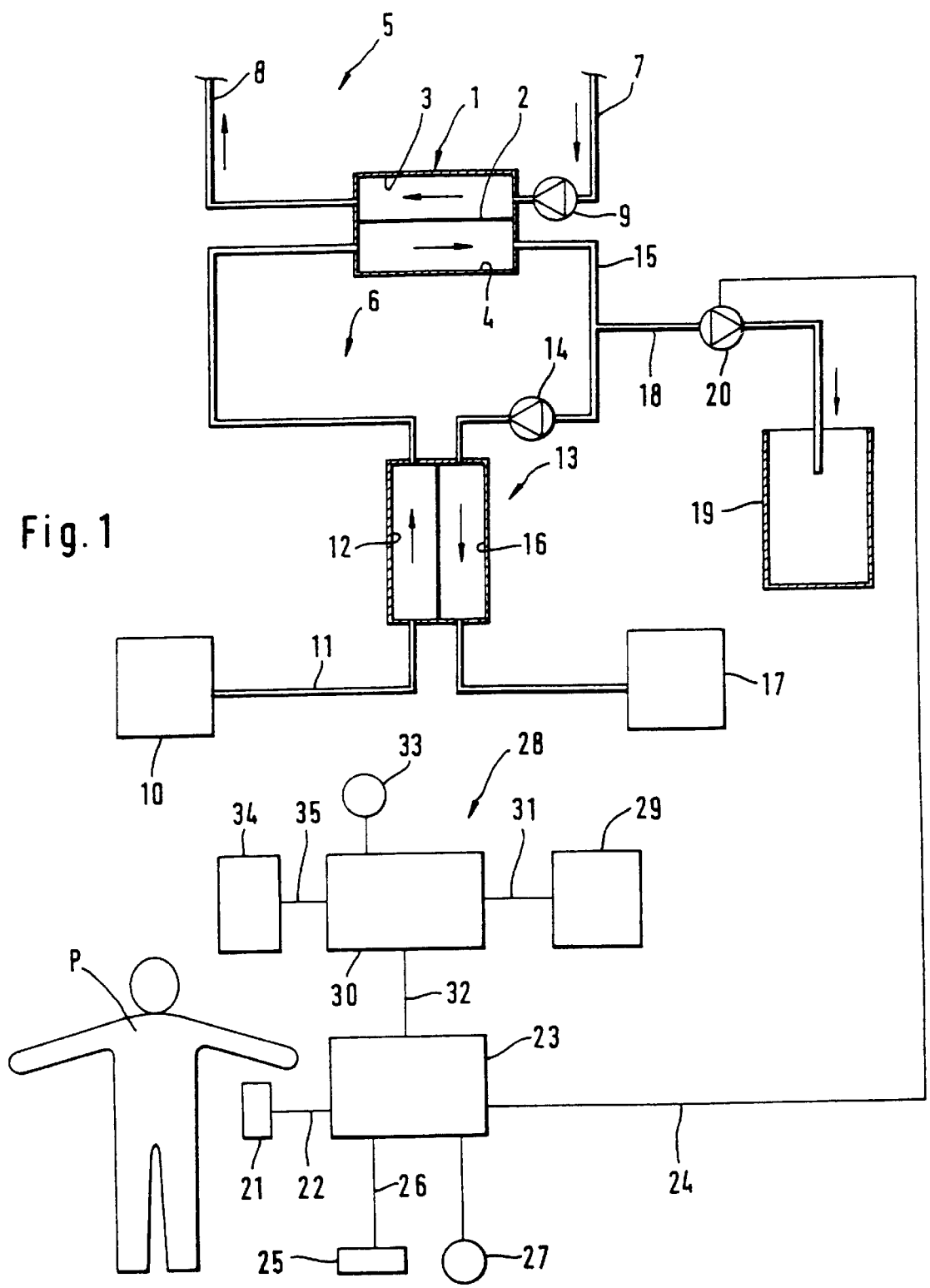
FIG. 1 shows a schematic diagram of a hemodiafiltration machine together with the safety device.

FIG. 1 shows a schematic diagram of a hemodiafiltration machine together with the safety device. The safety device may be part of a hemodiafiltration machine or a separate unit which is connected to an existing hemodiafiltration machine.

The hemodiafiltration machine has a dialyzer 1 which is divided by a semipermeable membrane 2 into a blood chamber 3 and a dialysis fluid chamber 4. Blood chamber 3 is connected to an extracorporeal blood circulation 5, and the dialysis fluid chamber 4 is connected to a dialysis fluid circuit 6. A blood inlet line 7 leads away from the patient to the inlet of blood chamber 3 of dialyzer 1, and a blood outlet line 8 leads from the outlet of the blood chamber back to the patient. A blood pump 9 is connected to blood inlet line 7.

A dialysis fluid inlet line 11 leads from a dialysis fluid source 10 to the inlet of the first balancing chamber 12 of a balancing unit 13 and from its outlet to the inlet of dialysis fluid chamber 4 of dialyzer 1.

A dialysis fluid outlet line 15 leads from the outlet of the dialysis fluid chamber to the second balancing chamber 16 of balancing unit 13 and from its outlet to a drain 17. Upstream from balancing unit 13, a dialysis fluid pump 14 is connected to dialysis fluid outlet line 15.

Upstream from the second balancing chamber 16 of balancing unit 13, an ultrafiltration line 18 branches off from dialysis fluid outlet line 15, leading to an ultrafiltrate container 19. An ultrafiltrate pump 20 is connected to the ultrafiltrate line 18 for removing the ultrafiltrate.

As long as ultrafiltrate pump 20 is not in operation, balancing unit 13 prevents a net exchange of fluid between primary circuit 5 and secondary circuit 6. No ultrafiltration takes place under these conditions. Ultrafiltration is started only when the ultrafiltrate pump is switched on, withdrawing fluid in a controlled manner from dialysis fluid chamber 4 of dialyzer 1 (ultrafiltration).

The blood treatment machine has a measurement unit 21 for determining the blood volume BV of patient P during hemodiafiltration. Measurement unit 21 is connected by a data line 22 to a control unit 23 which is in turn connected by a data line 24 to ultrafiltrate pump 20. In general, if measurement unit 21 makes available relative information regarding the blood volume of patient P, such as information on the water content in the patient's extracorporeal blood in line 7, that is sufficient for the safety device according to the present invention and for carrying out the method according to the present invention. Other measurement quantities that correlate with the relative blood volume can also be measured, such as the hemoglobin concentration or the protein concentration. An ultrasonic sensor may be used for this purpose.

For input of the total ultrafiltrate volume $UFV_{tot}$ which is to be withdrawn during the total treatment time, and for input of treatment time UFT plus optionally other patient-specific parameters, an input unit 25 is provided and is connected by a data line 26 to control unit 23. Control unit 23 adjusts the ultrafiltration rate UFR(t) of ultrafiltrate pump 20 as a function of blood volume BV of patient P as measured by measurement unit 21 in such a way that the predetermined total ultrafiltrate volume $UFV_{tot}$ is withdrawn during the predetermined treatment time UFT (blood volume control). Therefore, the control unit has a suitable control algorithm, which can be performed by a processor.

By operating a switch 27, control unit 23 can be deactivated, switching to manual adjustment of the ultrafiltration rate.

Safety device 28 prevents any risk to the patient due to faulty blood volume control. The safety device includes a computer unit 29 and a monitoring unit 30 which communicate with each other over a data line 31. The monitoring unit is connected by a data line 32 to control unit 23.

Computer unit 29 of safety device 28 determines an upper limit for ultrafiltration rate $UFR_{lim}$ from the predetermined total ultrafiltrate volume $UFV_{tot}$ and the predetermined treatment time UFT.

Safety device 28 can be deactivated by the user by operating a switch 33. This is appropriate in particular when, for example, a short-term increase in the ultrafiltration rate is necessary for measuring physiologically relevant parameters. (ultrafiltration bolus). This bolus volume can in turn be limited to an upper limit which is predetermined by the monitoring unit to further increase safety.

Figure 2:
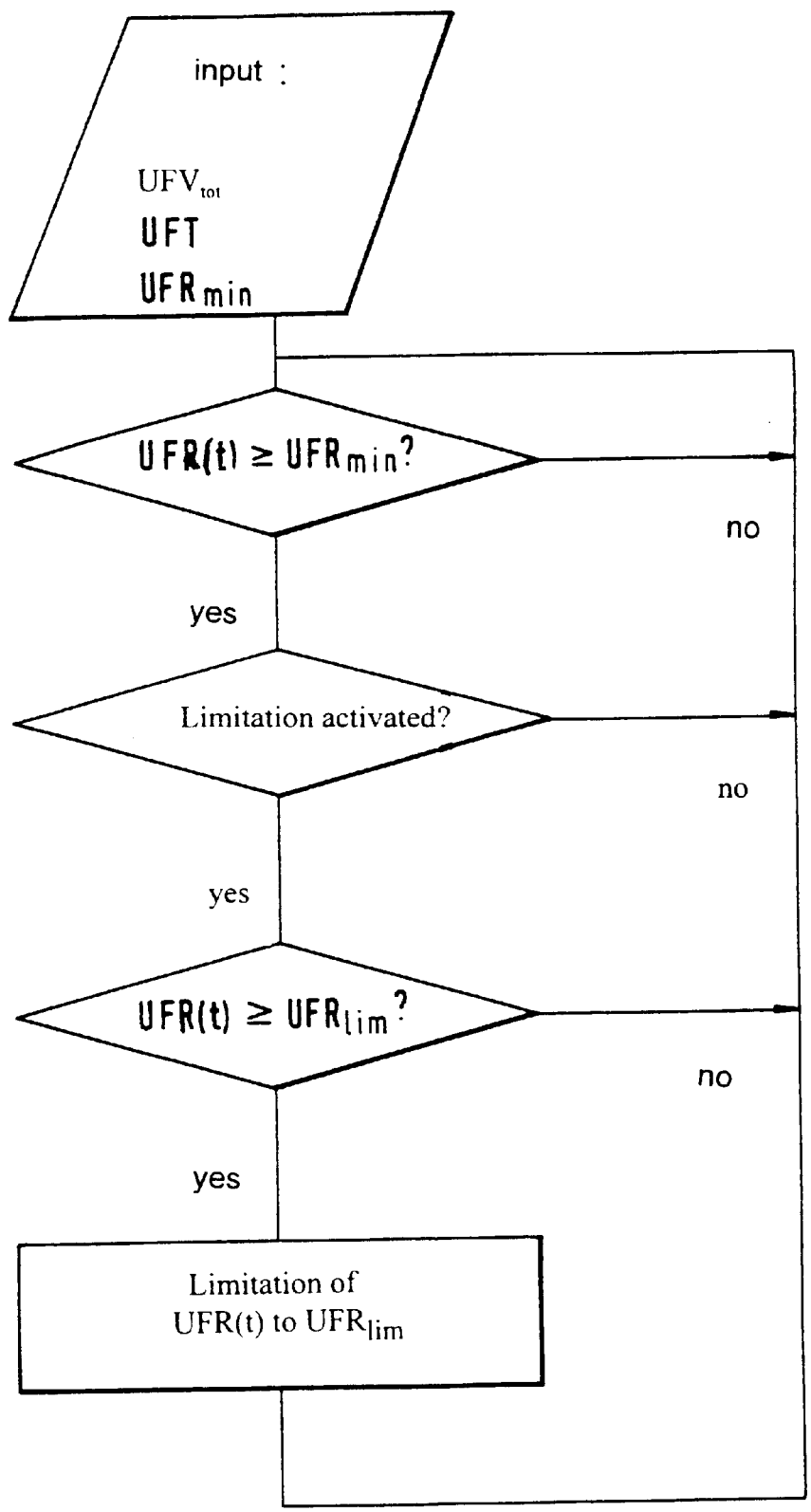
FIG. 2 shows the program sequence according to which the monitoring unit of the safety device functions.

FIG. 2 shows the program sequence according to which monitoring unit 29 of safety device 28 operates.

At the start of the treatment, the total ultrafiltrate volume $UFV_{tot}$, the treatment time UFT and a minimal ultrafiltration rate $UFR_{min}$ are entered on input unit 25 of the hemodiafiltration machine. The monitoring unit may also have its own input unit for this purpose. Patient-specific parameters $UFV_{tot}$, UFT and $UFR_{min}$ as well as the ultrafiltration rate UFR(t) controlled by control unit 23 are relayed to monitoring unit 29.

Monitoring unit 29 has a comparator device for comparing the ultrafiltration rate UFR(t) controlled by control unit 23 with the lower limit for ultrafiltration rate $UFR_{min}$. If UFR(t) is smaller than $UFR_{min}$, the ultrafiltration rate is not limited. If UFR(t) is greater than $UFR_{min}$, the monitoring unit will check whether the limitation on the ultrafiltration rate has been deactivated by the user. If the limitation has been activated, computer unit 29 determines an upper limit for ultrafiltration rate $UFR_{lim}$ which is compared in the monitoring unit with the ultrafiltration rate UFR(t) controlled by the control unit. If UFR(t) is greater than $UFR_{lim}$, the monitoring unit preselects the upper limit $UFR_{lim}$ as the ultrafiltration rate UFR(t). Only when the ultrafiltration rate controlled by the control unit drops below the upper limit does monitoring unit 29 terminate its intervention in control unit 23.

Determination of the upper limit for the ultrafiltration rate $UFR_{lim}$ is described in detail below.

Computer unit 29 of safety device 28 calculates the average ultrafiltration rate UFRM from the predetermined total ultrafiltrate volume $UFV_{tot}$ and the predetermined treatment time UFT according to the following equation:

$$UFRM = UFV_{tot}/UFT.$$

In a preferred embodiment, the computer unit has a processor for calculating the upper limit $UFR_{lim}$ from the average ultrafiltration rate UFRM as follows:

$$UFR_{lim} = \alpha * UFRM,$$

where $1.5 < \alpha < 2.3$.

This limit value remains constant during the treatment time. However, the upper limit $UFR_{lim}$ can also drop to the average ultrafiltration rate UFRM during the treatment time.

In a further preferred embodiment, the computer unit calculates the upper limit $UFR_{lim}$ according to the following equation:

$$UFR_{lim}(t, \alpha) = \left[\alpha \cdot UFRM - (\alpha - 1) \cdot UFRM \cdot \frac{t}{UFT}\right] \cdot \Phi\left(1 - \frac{t}{UFT}\right) + UFRM \cdot \Phi\left(\frac{t}{UFT} - 1\right)$$

where $\Phi(t)=0$ for $t<0$ and $\Phi(t)=1$ for $t \geq 0$.

Figure 3:
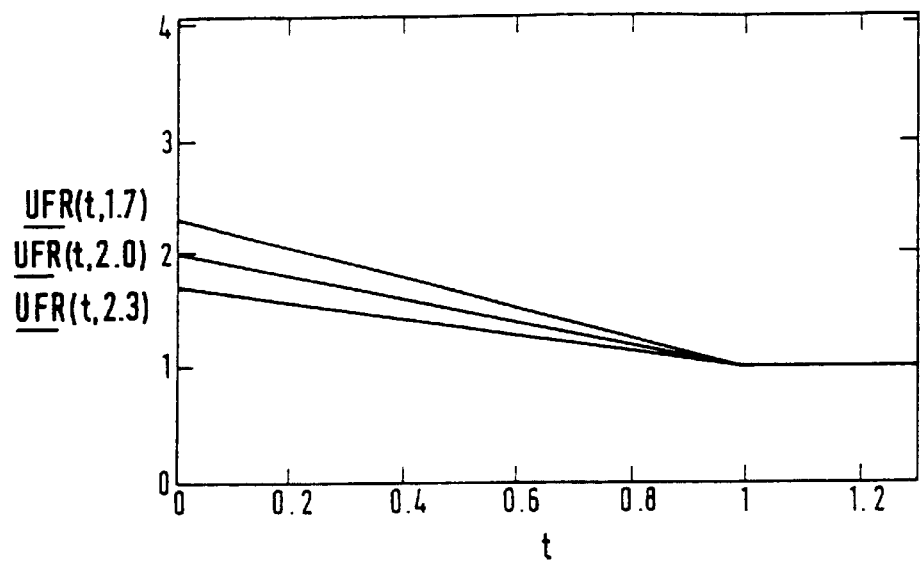
FIG. 3 shows the upper limit for ultrafiltration rate $UFR_{lim}$ as a function of the treatment time t of one embodiment of the safety device at which the upper limit decreases toward the end of the treatment.

FIG. 3 shows the upper limit for ultrafiltration rate $UFR_{lim}(t, \alpha)$ as a function of treatment time t, where the ordinate data refer to the average ultrafiltration rate UFRM and the abscissa data are based on treatment time UFT. The three curves differ by the parameter $\alpha = UFR_{lim}(0, \alpha)/UFRM$. At the beginning of the treatment, higher ultrafiltration rates are allowed (2 to 2.5 UFRM), but at most the average ultrafiltration rate UFRM is allowed toward the end of the treatment. The choice of a suitable parameter a is determined by the range of variation for the ultrafiltration rate which is needed by the control algorithm with which control unit 23 operates.

In the worst case of error, the blood volume control will always preselect the maximum allowed setpoint according to FIG. 3 without detecting the underlying cause of the error. Then the ultrafiltration volume is established as follows as a function of time:

$$UFV(t, \alpha) = \alpha \cdot UFRM \cdot t - (\alpha - 1) \cdot \frac{t^2}{2 \cdot UFT}$$

Figure 4:
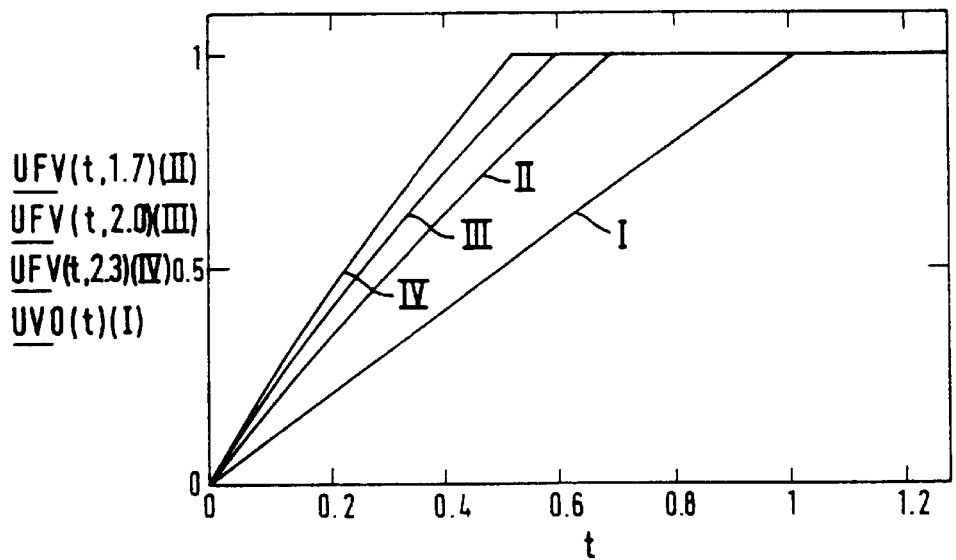
FIG. 4 shows the ultrafiltrate volume UFV as a function of the treatment time t in the worst case of error under the limitation of the ultrafiltration rate according to the embodiment in FIG. 3.

Curve I in FIG. 4 indicates the ultrafiltration volume at a constant ultrafiltration rate (UFR=UFRM), with the ordinate data being standardized to the total ultrafiltrate volume $UFV_{tot}$ and the abscissa data being standardized to the treatment time UFT. In the worst case of error, the ultrafiltrate volume UFV(t, $\alpha$) increases to an end value of 1 in approximately half the time according to one of the curves II, III, IV (depending on $\alpha$).

In another preferred embodiment, the upper limit for the ultrafiltration rate $UFR_{lim}$ is based on the residual ultrafiltration rate UFRR(t), which is calculated in the computer unit according to the following equation:

$$UFRR(t, \alpha) = (UFV_{tot} - UFV(t))/(UFT - t)$$

The computer unit calculates the upper limit from the residual ultrafiltration rate UFRR(t) as follows:

$$UFR_{lim}(t, \alpha) = \alpha * UFRR(t),$$

where $1 < \alpha < 2.3$.

Figure 5:
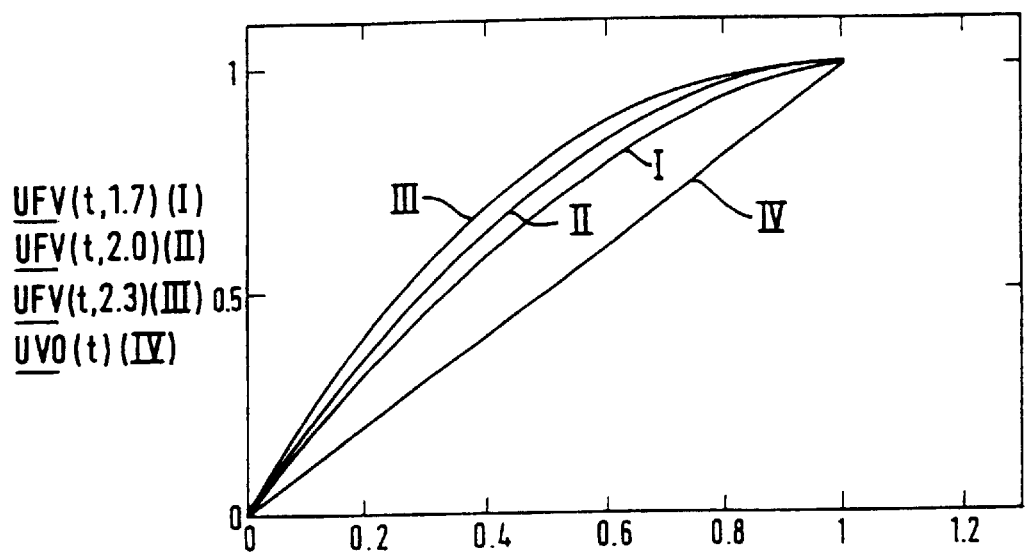
FIG. 5 shows the ultrafiltrate volume UFV as a function of the treatment time t in the worst case of error in another embodiment of the safety device.

FIG. 5 shows the ultrafiltrate volume UFV(t, $\alpha$) as a function of the treatment time t, with the ordinate data being standardized to the total ultrafiltrate volume $UFV_{tot}$ and the abscissa data being standardized to the treatment time UFT. FIG. 5 shows the increase in ultrafiltrate volume $UFV(t, \alpha)$ which is even flatter in comparison with FIG. 4 and is obtained under worst case conditions, e.g., when there is an unrecognized failure of the blood volume control at the beginning of the treatment, when the ultrafiltration rate is limited by the monitoring unit.

In addition to the above components, the safety device also has a warning device 34 which is connected by a data line 35 to monitoring unit 30 and has two acoustic and/or optical warning signals.

The warning device has a comparator device which compares the residual ultrafiltration rate UFRR(t) with the average ultrafiltration rate UFRM. After the average ultrafiltration rate UFRM is exceeded, the warning device delivers an acoustic warning signal and/or an optical warning signal to alert the user to the fact that it might not be possible to withdraw the predetermined total ultrafiltrate volume $UFV_{tot}$ within treatment time UFT and thus the dry weight might not be reached.

Control unit 23 adjusts the ultrafiltration rate UFR(t) in such a way that UFR(t) is greater than the average ultrafiltration rate UFRM. Under normal conditions, the residual ultrafiltration rate UFRR(t) then runs below UFRM for the entire treatment time. The warning signal is delivered either immediately after exceeding the average ultrafiltration rate UFRM, after a predetermined period of time, e.g., five minutes, has elapsed, after exceeding a certain tolerance limit UFRM+αUFR or after exceeding a certain integrated ultrafiltration quantity.

The comparator device of warning device 34 also compares the residual ultrafiltration rate UFRR(t) with the upper limit for the ultrafiltration rate $UFR_{lim}$. If the residual ultrafiltration rate UFRR is greater than the upper limit $UFR_{lim}$, the warning device delivers another acoustic and/or optical warning signal, alerting the user to the fact that the dry weight can no longer be reached with the monitoring unit activated.

Figure 6:
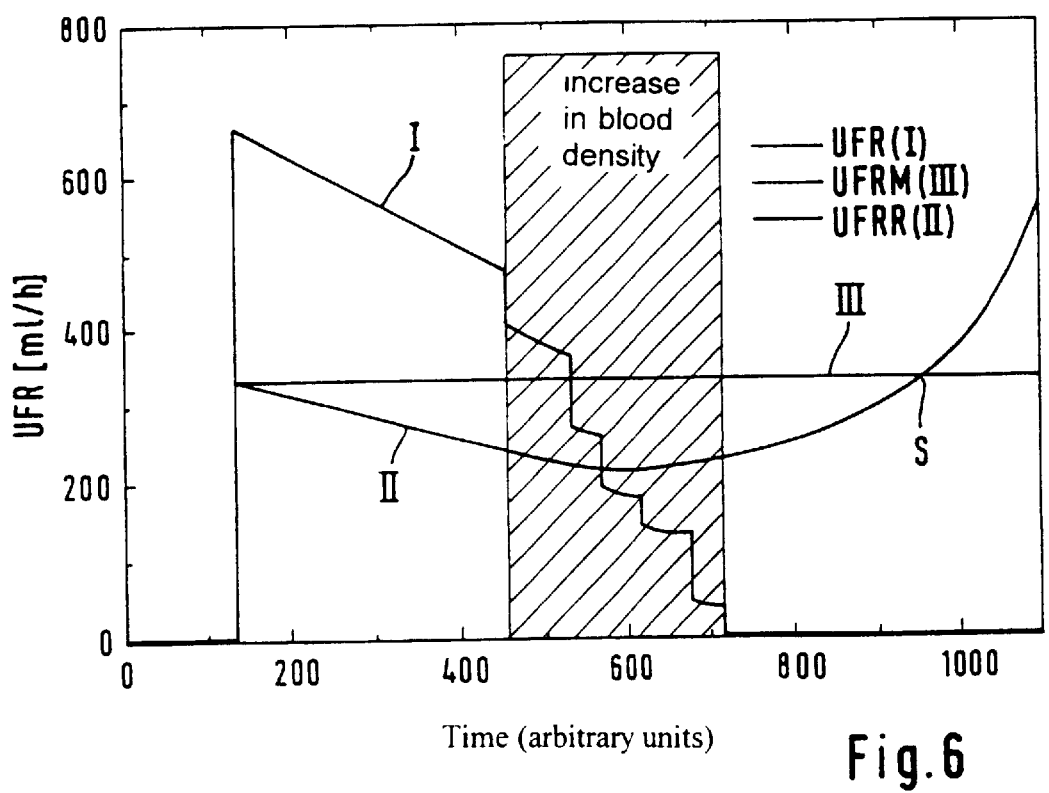
FIG. 6 shows the ultrafiltration rate UFR, the average ultrafiltration rate UFRM and the residual ultrafiltration rate UFRR as a function of the treatment time t.

FIG. 6 shows the case where the control unit selects a very low ultrafiltration rate UFR (curve I). e.g., on the basis of an error during the treatment (shaded area). In this case, there is an increase in the residual ultrafiltration rate UFRR which is necessary for withdrawing the volume still remaining in the remaining treatment time (curve II). The point of intersection between the residual ultrafiltration rate UFRR and the average ultrafiltration rate UFRM (curve III) is labeled as S in FIG. 6.

What is claimed is:

1. A safety device for an extracorporeal blood treatment machine having a blood inlet line leading from a patient to an inlet of a first chamber of an exchange unit divided by a semipermeable membrane into the first chamber and a second chamber and a blood outlet line leading from an outlet of the first chamber to the patient, the treatment machine including an ultrafiltration device for withdrawing a predetermined total ultrafiltrate volume from the second chamber at an ultrafiltration rate during a predetermined treatment time, a measurement unit for determining a blood volume or a measurement quantity of the patient correlating with the blood volume, and a control unit for controlling the ultrafiltration rate as a function of the blood volume, the safety device comprising:

a computer unit for determining an upper limit for the ultrafiltration rate as a function of the predetermined total ultrafiltrate volume and the predetermined treatment time; and a monitoring unit for limiting the ultrafiltration rate to the upper limit.

2. The safety device according to claim 1 wherein the computer unit includes a processor for determining an average ultrafiltration rate as a function of the predetermined total ultrafiltrate volume and the predetermined treatment time, the upper limit being determined by multiplying the average ultrafiltration rate by a factor α.

3. The safety device according to claim 1 wherein the control unit has a processor for reducing the ultrafiltration rate as a treatment time increases.

4. The safety device according to claim 1 wherein the computer unit includes a processor for reducing the upper limit of the ultrafiltration rate with an increase in ultrafiltrate volume.

5. The safety device according to claim 1 wherein the computer unit includes a processor for determining an average ultrafiltration rate as a function of the predetermined total ultrafiltrate volume and the predetermined treatment time, and the upper limit at a certain time t can be determined according to the following equation:

$$UFR_{\lim}(t, \alpha) = \left[\alpha \cdot UFRM - (\alpha - 1) \cdot UFRM \cdot \frac{t}{UFT}\right] \cdot \Phi\left(1 - \frac{t}{UFT}\right) + UFRM \cdot \Phi\left(\frac{t}{UFT} - 1\right)$$

where $\Phi(t)=0$ for $t<0$ and $\Phi(t)=1$ for $t \geq 0$, UFRM is the average ultrafiltration rate, UFT is the predetermined treatment time and α is a factor.

6. The safety device according to claim 1 wherein the computer unit has a processor for determining a residual ultrafiltration rate at which the ultrafiltrate volume can be withdrawn at a certain time within the period of time still available for the treatment time UFT as a function of the predetermined total ultrafiltrate volume $UFV_{tot}$ and the predetermined treatment time UFT according to the following equation:

$$UFRR(t)=(UFV_{tot}-UFV(t))/(UFV-t)$$

and the upper limit at the time t can be determined by multiplying the residual ultrafiltration rate UFRR(t) by a factor α, wherein $1<\alpha<2.3$.

7. The safety device according to claim 6 further comprising a warning device, the warning device having a comparator device for comparing the residual ultrafiltration rate UFRR(t) with an average ultrafiltration rate and for delivering a warning signal if the average ultrafiltration rate is exceeded.

8. The safety device according to claim 6 further comprising a warning device, the warning device including a comparator device for comparing the residual ultrafiltration rate UFRR(t) with the upper limit, the warning device for delivering a warning signal if the upper limit is exceeded.

9. The safety device according to claim 1 wherein the monitoring unit includes a comparator device for comparing the ultrafiltration rate controlled by the control unit with a lower limit for the ultrafiltration rate, the ultrafiltration rate being limited to the upper limit only when the ultrafiltration rate is greater than the lower limit.

10. A method of increasing the safety of an extracorporeal blood treatment machine having a blood inlet line leading from a patient to the inlet of a first chamber of an exchange unit divided by a semipermeable membrane into the first chamber and a second chamber, and a blood outlet line leading from an outlet of the first chamber to the patient, the treatment machine including an ultrafiltration device for withdrawing a predetermined total ultrafiltrate volume from the second chamber of the exchange unit at an ultrafiltration rate during a predetermined treatment time, a measurement unit for determining a blood volume or a measurement quantity of the patient which correlates with the blood volume, and a control unit for controlling an ultrafiltration rate as a function of the blood volume, the method comprising the steps of:

determining an upper limit for the ultrafiltration rate as a function of the predetermined total ultrafiltrate volume and the predetermined treatment time; and limiting the ultrafiltration rate to the upper limit.

11. The method according to claim 10 further comprising determining an average ultrafiltration rate by forming a quotient of the predetermined total ultrafiltrate volume and the predetermined treatment time, and wherein the upper limit is determined by multiplying the average ultrafiltration rate by a factor $\alpha$.

12. The method according to claim 11 wherein the upper limit for the ultrafiltration rate decreases with increasing treatment time.

13. The method according to claim 11 wherein the upper limit for the ultrafiltration rate decreases with increasing ultrafiltrate volume.

14. The method according to claim 10 further comprising determining an average ultrafiltration rate by forming a quotient from the predetermined total ultrafiltrate volume and the predetermined treatment time, and the upper limit $UFR_{lim}(t, \alpha)$ at a certain time t being determined according to the following equation:

$$UFR_{\lim}(t, \alpha) = \left[\alpha \cdot UFRM - (\alpha - 1) \cdot UFRM \cdot \frac{t}{UFT}\right] \cdot \Phi\left(1 - \frac{t}{UFT}\right) + UFRM \cdot \Phi\left(\frac{t}{UFT} - 1\right)$$

where $\Phi(t)=0$ for $t<0$ and $\Phi(t)=1$ for $t \geq 0$, UFRM is the average ultrafiltration rate, UFT is the predetermined treatment time and $\alpha$ is a factor.

15. The method according to claim 10 further comprising determining a residual ultrafiltration rate UFRR(t) at which the ultrafiltrate volume UFV can be withdrawn at a certain time within the period of the treatment time UFT still available as a function of the predetermined total ultrafiltrate volume $UFV_{tot}$ and the predetermined treatment time UFT according to the following equation:

$$UFRR(t)=(UFV_{tot}-UFV(t))/(UFT-t)$$

and the upper limit being determined by multiplying the residual ultrafiltration rate UFRR(t) by a factor $\alpha$, wherein $1<\alpha<2.3$.

16. The method according to claim 15 further comprising comparing the residual ultrafiltration rate UFRR(t) with the average ultrafiltration rate, and delivering a warning signal if the average ultrafiltration rate is exceeded.

17. The method according to claim 15 further comprising comparing the residual ultrafiltration rate UFRR(t) with the upper limit and delivering a warning signal if the upper limit is exceeded.

18. The method according to claim 10 further comprising comparing the predetermined ultrafiltration rate with a lower limit for the ultrafiltration rate, and limiting the ultrafiltration rate to the upper limit only when the ultrafiltration rate is greater than the lower limit.

19. An extracorporeal blood treatment machine comprising:

an exchange unit divided by a semipermeable membrane into a first chamber and a second chamber;

a blood inlet line leading from a patient to an inlet of the first chamber and a blood outlet line leading from an outlet of the first chamber to the patient;

an ultrafiltration device for withdrawing a predetermined total ultrafiltrate volume from the second chamber at an ultrafiltration rate during a predetermined treatment time;

a measurement unit for determining a blood volume or a measurement quantity of the patient correlating with the blood volume;

a control unit for controlling the ultrafiltration rate as a function of the blood volume; and a safety device including a computer unit for determining an upper limit for the ultrafiltration rate as a function of the predetermined total ultrafiltrate volume and the predetermined treatment time and a monitoring unit for limiting the ultrafiltration rate to the upper limit.

20. The extracorporeal blood treatment machine according to claim 19 further comprising a warning device for delivering a warning signal if the upper limit is exceeded.

21. A method for an extracorporeal blood treatment for a patient comprising the steps of:

passing blood from a patient through a first chamber of an exchange unit and back to the patient, the exchange unit being divided by a semipermeable membrane into the first chamber and a second chamber;

withdrawing a predetermined total ultrafiltrate volume from the second chamber at an ultrafiltration rate during a predetermined treatment time;

determining a blood volume or a measurement quantity of the patient which correlates with the blood volume;

controlling the ultrafiltration rate as a function of the blood volume;

determining an upper limit for the ultrafiltration rate as a function of the predetermined total ultrafiltrate volume and the predetermined treatment time; and limiting the ultrafiltration rate to the upper limit.

22. The method according to claim 21 further comprising determining an average ultrafiltration rate by forming a quotient of the predetermined total ultrafiltrate volume and the predetermined treatment time, and wherein the upper limit is determined by multiplying the average ultrafiltration rate by a factor $\alpha$.

23. The method according to claim 21 wherein the upper limit for the ultrafiltration rate decreases with increasing treatment time.

24. The method according to claim 21 wherein the upper limit for the ultrafiltration rate decreases with increasing ultrafiltrate volume.

* * * * *

UNITED STATES PATENT AND TRADEMARK OFFICE
CERTIFICATE OF CORRECTION

PATENT NO. : 6,602,424 B1  
DATED : August 5, 2003  
INVENTOR(S) : Kramer et al.

It is certified that error appears in the above-identified patent and that said Letters Patent is hereby corrected as shown below:

Column 8,
Line 40, change "/(UFV-t)" to -- /(UFT-t) --.

Signed and Sealed this

Seventeenth Day of February, 2004

JON W. DUDAS  
*Acting Director of the United States Patent and Trademark Office*